United States Patent
Galbierz et al.

(10) Patent No.: US 11,007,085 B2
(45) Date of Patent: May 18, 2021

(54) ADHESIVE THERAPEUTIC COVER

(71) Applicants: Thomas R. Galbierz, Brentwood, TN (US); Michael A. Galbierz, St. Louis, MO (US)

(72) Inventors: Thomas R. Galbierz, Brentwood, TN (US); Michael A. Galbierz, St. Louis, MO (US)

(73) Assignees: Thomas R. Galbierz, Brentwood, TN (US); Miachael A. Galbiert, St. Louis, MO (US)

( * ) Notice: Subject to any disclaimer, the term of this patent is extended or adjusted under 35 U.S.C. 154(b) by 676 days.

(21) Appl. No.: 15/561,924

(22) PCT Filed: Mar. 30, 2016

(86) PCT No.: PCT/US2016/025017
§ 371 (c)(1),
(2) Date: Sep. 26, 2017

(87) PCT Pub. No.: WO2016/160997
PCT Pub. Date: Oct. 6, 2016

(65) Prior Publication Data
US 2018/0110659 A1    Apr. 26, 2018

Related U.S. Application Data

(60) Provisional application No. 62/142,266, filed on Apr. 2, 2015.

(51) Int. Cl.
*A61F 13/02* (2006.01)
*A61F 13/00* (2006.01)
(Continued)

(52) U.S. Cl.
CPC .... *A61F 13/0233* (2013.01); *A61F 13/00051* (2013.01); *A61F 13/00063* (2013.01);
(Continued)

(58) Field of Classification Search
CPC .......... A61F 13/02; A61F 13/0246; A61F 2013/00089; A61F 5/00; A61F 5/03;
(Continued)

(56) References Cited

U.S. PATENT DOCUMENTS

| 4,616,644 A | 10/1986 | Saferstein et al. |
| 4,884,563 A | 12/1989 | Sessions |

(Continued)

FOREIGN PATENT DOCUMENTS

| WO | 2014120746 A1 | 8/2014 |
| WO | 2016122892 A1 | 8/2016 |

OTHER PUBLICATIONS

International Search Report for corresponding PCT/US2016/025017 dated Jun. 30, 2016.
(Continued)

*Primary Examiner* — Ophelia A Hawthorne
(74) *Attorney, Agent, or Firm* — Sandberg Phoenix & von Gontard, P.C.

(57) ABSTRACT

An adhesive therapeutic cover comprises at least one lift device and a single sheet of at least a two-ply material that includes a cover material with an adhesive on a bottom surface and a backing layer. The cover material defines at least one opening therethrough or at least one opening area which is removable after application of the cover material to a patient to form an opening through the cover material. The at least one lift device comprises a connector adhered or adherable to the cover material in alignment with the opening or opening area. The connector can be connected to a pressurized source of a flowable lifting agent, to urge the flowable lifting agent through the connector and the opening to separate the cover material from patient skin. Sensors can (Continued)

be provided to monitor and/or control the flow of lifting agent through the lifting device during removal of the cover from the patient.

46 Claims, 4 Drawing Sheets (51) Int. Cl.
| | |
|---|---|
| B32B 3/08 | (2006.01) |
| A61L 15/58 | (2006.01) |
| B32B 27/10 | (2006.01) |
| B32B 7/02 | (2019.01) |
| B32B 3/26 | (2006.01) |
| B32B 5/02 | (2006.01) |
| B32B 27/36 | (2006.01) |
| B32B 3/10 | (2006.01) |
| B32B 29/00 | (2006.01) |
| A61L 31/04 | (2006.01) |
| A61L 31/14 | (2006.01) |
| A61N 5/06 | (2006.01) |

(52) U.S. Cl.
CPC ...... *A61F 13/0236* (2013.01); *A61F 13/0246* (2013.01); *A61L 15/58* (2013.01); *A61L 31/04* (2013.01); *A61L 31/14* (2013.01); *A61N 5/0616* (2013.01); *B32B 3/08* (2013.01); *B32B 3/10* (2013.01); *B32B 3/266* (2013.01); *B32B 5/024* (2013.01); *B32B 7/02* (2013.01); *B32B 27/10* (2013.01); *B32B 27/36* (2013.01); *B32B 29/002* (2013.01); *A61F 2013/00119* (2013.01); *A61F 2013/00157* (2013.01); *A61F 2013/00174* (2013.01); *B32B 2255/10* (2013.01); *B32B 2255/12* (2013.01); *B32B 2255/26* (2013.01); *B32B 2262/062* (2013.01); *B32B 2307/54* (2013.01); *B32B 2307/546* (2013.01); *B32B 2307/7145* (2013.01); *B32B 2307/724* (2013.01); *B32B 2307/7265* (2013.01); *B32B 2307/732* (2013.01); *B32B 2556/00* (2013.01)

(58) Field of Classification Search
CPC .... A61F 5/055; A61F 5/05816; A61F 5/3707; A61F 5/012; A61F 5/05891; A61F 5/05883; A61F 5/024; A61F 5/026; A61F 5/028; A61F 13/12; A61F 2007/0009; A61M 1/0088; A61M 27/00; A61M 1/0031; A61M 1/0023; A61M 1/0096; A61M 1/0058; A61M 2209/088; A61M 1/009; A61M 2205/3331; A61M 1/0072; A61M 3/0216; A61M 1/0011; A61M 2205/581; A61M 2205/583; A61M 1/0066; A61M 1/0068; A61M 1/008; A61M 2205/075; A61M 35/00; A61M 39/24; A61M 1/00; A61M 1/0005; A42B 3/0473; A47C 7/383
See application file for complete search history.

(56) References Cited

U.S. PATENT DOCUMENTS

| | | | | |
|---|---|---|---|---|
| 7,338,482 | B2 * | 3/2008 | Lockwood | ......... A61M 1/0084 601/6 |
| 8,162,907 | B2 | 4/2012 | Heagle | |
| 8,212,100 | B2 * | 7/2012 | Moore | ............... A61F 13/0246 602/43 |
| 8,246,591 | B2 | 8/2012 | Braga et al. | |
| 8,597,689 | B2 | 12/2013 | Archambeau et al. | |
| 8,784,392 | B2 | 7/2014 | Vess et al. | |
| 8,946,499 | B2 * | 2/2015 | Iyer | ........................ A61L 15/44 602/41 |
| 2005/0137539 | A1 * | 6/2005 | Biggie | ............... A61M 1/0096 604/313 |
| 2005/0159711 | A1 * | 7/2005 | Kathrani | ........... A61B 17/3421 604/264 |
| 2010/0160901 | A1 | 6/2010 | Hu et al. | |
| 2013/0165821 | A1 | 6/2013 | Freedman et al. | |
| 2014/0343520 | A1 | 11/2014 | Bennett et al. | |

OTHER PUBLICATIONS

Written Opinion for corresponding PCT/US2016/025017 dated Jun. 30, 2016.
International Preliminary Report on Patentability for corresponding PCT/US2016/025017 dated Dec. 27, 2016.
Rippon, White and Davies, Skin Adhesives and Their Role in Wound Dressings, Wounds UK 2007, vol. 3, No. 4, pp. 76-86.

* cited by examiner

ADHESIVE THERAPEUTIC COVER

CROSS-REFERENCE TO RELATED APPLICATIONS

This application is the US National Stage under 35 U.S.C. § 371 of International App. No. PCT/US2016/025017, which claims priority to U.S. App. No. 62/142,266 filed Apr. 2, 2015 for "Adhesive Therapeutic Cover With Removal Device". Both said applications are incorporated herein by reference.

STATEMENT REGARDING FEDERALLY SPONSORED RESEARCH OR DEVELOPMENT

Not Applicable.

BACKGROUND

This application relates to adhesive therapeutic covers, such as bandages, medical drapes, and the like, and in particular to such covers wherein the covers are provided with ports adapted to connect the cover to sources of pressurized gas and/or fluids and sensors to monitor various parameters in the area of the cover in proximity to the port.

Approximately 1.5 million patients acquire injuries to the skin caused by tape/bandage removal annually. Elderly and/or sick patients require repeated taping over the same area, making them highly susceptible to dermis stripping from bandage removal.

Adhesive therapeutic covers, such as bandages and drapes, have long been used to cover wounds. However, such covers can be painful to remove, especially for sensitive skin or previously damaged skin, or if the bandage is covering body hair (such as arm hair or leg hair). Thus, for example, adhesive bandages are not applied to burn victims or skin grafts for fear of damaging newly formed skin.

In addition, adhesive therapeutic covers can include retractors, such as disclosed in WO 2014/120746, which is incorporated herein by reference, which can be used to reposition or retract a patient's excess flesh (such as a panniculus) to facilitate certain medical or surgical procedures. Such retractors are comprised of large sheets of adhesive film which are adhered to the patient's skin and which can be painful to the patient to remove.

It would be desirable to provide an adhesive therapeutic cover which would facilitate removal of the adhesive therapeutic cover to thereby reduce the likelihood of damage to skin during removal and to make removal of adhesive therapeutic cover less painful for the patient.

BRIEF SUMMARY

Briefly stated, a therapeutic cover is provided which is adherable to the patient and provided with means, or is otherwise adapted, so that the cover can be separated from the patient's skin with as little trauma or damage to the patient's skin as possible. The cover comprises a single sheet of at least a two-ply material and at least one connector adapted to be connected to a pressurized source of a flowable lifting agent. The material includes a cover material (which itself can comprise 1, 2 or more plies) and a backing layer. The cover material has an adhesive applied to a bottom surface thereof to removably adhere the cover material and backing layer together. The cover material defines at least one opening therethrough or has at least one opening area which can be removed or opened after application of the cover material to a patient to form an opening through the cover material.

Depending on the size and shape of the cover, the opening can be positioned approximately midway between opposite sides of the bottom portion of the cover material. The cover can also include multiple openings.

The connector, which will be manufactured with various diameters, is adhered to the cover material in alignment with the opening or opening area adapted to extend upwardly from a top surface of the cover material, such that the flowable lifting agent can be urged through the connector and the opening in the cover material to separate the cover material from patient skin after application of the cover material to patient skin.

In accordance with an aspect of the cover, the cover material is comprised of a manmade material, natural material, or combination thereof. The material, further can be breathable or non-breathable material. In accordance with an aspect of the cover, the cover material is formed from a thermoplastic elastomer, such as a polyester or a polyurethane.

In accordance with an aspect of the cover, the cover material can vary in thickness, but typically is about 1.2 mils (0.0012" or about 0.03 mm).

In accordance with an aspect of the cover, the adhesive should have an adhesive strength sufficiently low so as to substantially prevent trauma to human skin when the cover material is removed from human skin, i.e., the higher the adhesive strength, the higher the surface tension and, thus, the higher the probability of causing tissue damage. Typically, the adhesive has a strength of about 10 oz/in to about 50 oz/in.

In accordance with an aspect of the cover, the connector port is mounted to, or adapted to be mounted to, the cover material.

In accordance with an aspect of the cover, the flowable lifting agent is a gas, liquid, flowable gel, or a combination thereof. The lifting agent can comprise a medicament and/or a skin treating agent.

In accordance with an aspect of the cover, the lift device may or may not comprise an apron which surrounds the connector port and flange, and to which the connector port is fixed. In this instance, the apron is fixed to the cover material. The apron is adhered to the cover material by an adhesive or bond which is stronger than the adhesive of the cover material.

In accordance with an aspect of the cover, the apron is made of a material having an elongation factor that is less than an elongation factor of the cover material. For example, the apron has an elongation factor that is no more than about 75% of the elongation factor of the top layer. Alternatively, the apron can have an elongation factor of about 0% to about 200%.

In accordance with an aspect of the cover, the apron is secured to the cover material by an apron adhesive or bond which is a stronger adhesive than the adhesive on the bottom surface of the cover material.

In accordance with an aspect of the cover, the strength of the apron adhesive or bond is at least equal to or greater than the strength of the cover material adhesive.

In accordance with an aspect of the cover, the cover further includes a border extending around the periphery of the cover material. The border can be comprised of a material that is adhered to the cover material. The border is at least as thick as the cover material, and preferably has a thickness greater than the thickness of the cover material. For example, the border can be approximately 1× to 2× as thick as the cover material.

In accordance with an aspect of the cover, the material from which the border is made has an elongation factor that is less than the elongation factor of the cover material.

In accordance with an aspect of the cover, the border is about 0.5" (~1.3 cm) to about 3" (~7.5 cm) wide.

As an alternative to the border, the cover can be provided with two different adhesives, a weaker adhesive throughout most of the cover, and a stronger adhesive around the periphery of the cover. This stronger adhesive around the periphery will result in a higher surface tension along the periphery of the cover, and thus would replace the border, described above. That is, the border would be formed from a stronger adhesive, rather than a second ply of material.

In accordance with an aspect of the cover, the material from which the border is made is a non-breathable material.

Removal of the therapeutic cover from a patient using the lifting device comprises introducing a flowable lifting agent through an aperture in the cover between the therapeutic cover and the patient's skin at a rate and pressure sufficient to substantially eliminate the possibility of damaging or injuring the patient's skin while removing the adhesive therapeutic cover.

In accordance with an aspect of the method, the lifting agent can be introduced at a pressure of about 2-4 psi as to dissipate the energy of the adhesive bond which holds the cover to the patient's dermis.

In accordance with an aspect of the method, the lifting agent is a gas, a liquid, a flowable gel or a combination thereof. The lifting agent can contain medicaments and/or skin treating agents.

In accordance with another aspect of the cover, the cover may include a series of circuit boards with sensors that monitor/collect and transmit data relative to monitored parameters, such as flow rate of the lifting agent through the lifting device, the extent of distribution of the lifting agent under the cover, the pressure between the patient's skin and the lifting device as lifting agent is passed through the lifting device, and ambient and physiological aspects of the patient's wound. These monitors/sensors are wired or wireless and can be integral with the cover or placed at desired locations when the cover is applied to the patient, such as in close proximity to the target site, proximate the lift device, and proximate the edge of the cover.

Positive pressure creates a mechanism to separate the adhesive from the dermis. This process creates less tissue damage and subsequent pain for the patient. Since the tissues surrounding a wound tend to be compromised, this modality of removal is optimal. Positive pressurization minimizes dermal stripping.

BRIEF DESCRIPTION OF THE DRAWINGS

Corresponding reference numerals will be used throughout the several figures of the drawings.

DETAILED DESCRIPTION

The following detailed description illustrates the claimed invention by way of example and not by way of limitation. This description will clearly enable one skilled in the art to make and use the claimed invention, and describes several embodiments, adaptations, variations, alternatives and uses of the claimed invention, including what we presently believe is the best mode of carrying out the claimed invention. Additionally, it is to be understood that the claimed invention is not limited in its application to the details of construction and the arrangements of components set forth in the following description or illustrated in the drawings. The claimed invention is capable of other embodiments and of being practiced or being carried out in various ways. Also, it is to be understood that the phraseology and terminology used herein is for the purpose of description and should not be regarded as limiting.

The adhesive therapeutic cover of the invention is described with respect to a bandage. However, it will be understood that the adhesive therapeutic cover also encompasses retractors, such as described in WO 2014/120746, as well as adhesive films that are applied to a patient's skin during, or in conjunction with, cosmetic or surgical procedures, or after such procedures, including wound exposure devices, such as disclosed in International App. No. PCT/US2016/013404, entitled "Wound Exposure Device For Use With Patients Having Excessive And/Or Redundant Tissue And Method Of Use," which was filed on Jan. 14, 2016, and which is incorporated herein by reference.

Figure 1:
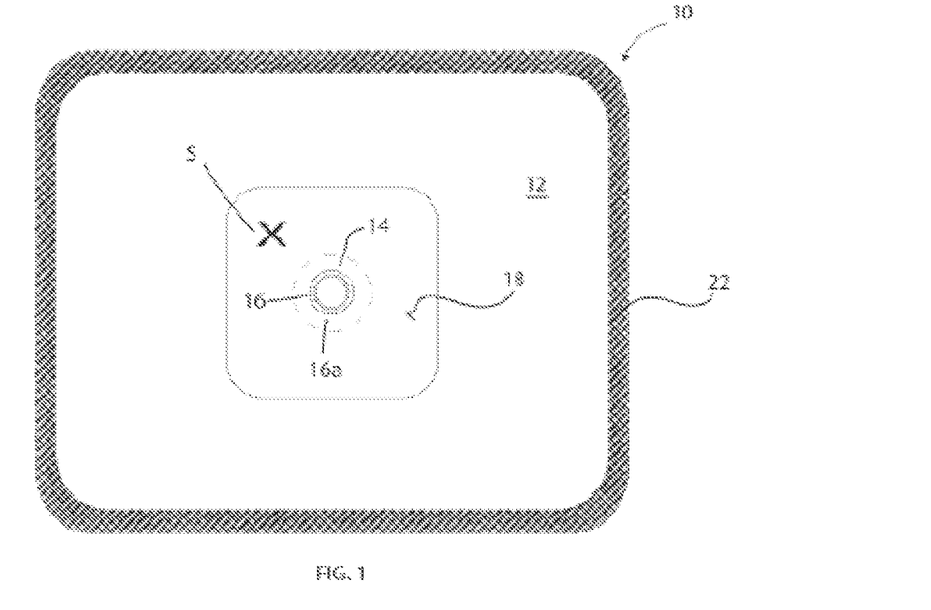
FIG. 1 is a plan view of an adhesive therapeutic cover in the form of a bandage with a lift device to facilitate removal of the bandage from a patient.
Figure 2:
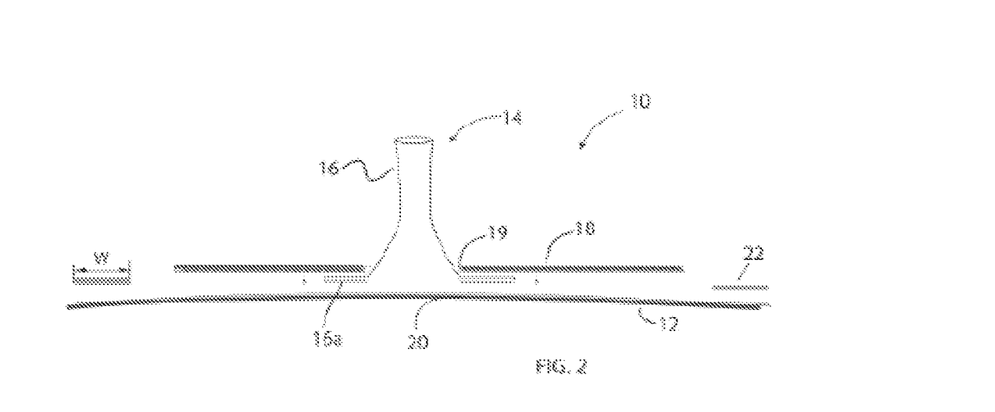
FIG. 2 is an exploded cross-sectional view of the adhesive therapeutic cover.
Figure 3A:
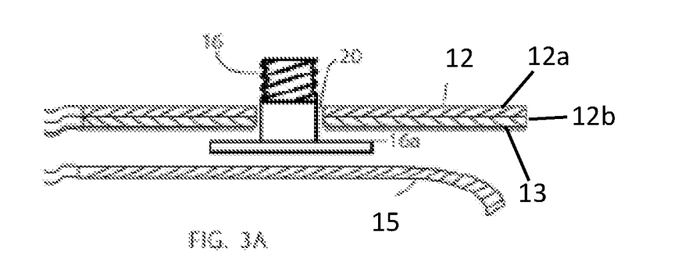
FIG. 3A is a cross-sectional view of a second embodiment of the lift device, demonstrating a first method of securing the lift device to the cover.

An adhesive therapeutic cover 10, in the form of a bandage, is shown generally in plan FIG. 1 and in schematic cross-section in FIG. 2. The bandage 10 comprises a main, or top, layer 12. The layer 12, as shown in FIG. 3A, is comprised of a cover material having a top surface and a bottom surface. An adhesive 13 is applied to substantially the entire bottom surface of the cover material, and a peel-away coating 15 (such as a paper coating) is adhered to the bottom surface of the cover material to be peeled away from the cover material when the bandage 10 is applied to a patient. As shown in FIG. 3A, the cover material 12 can comprise a first ply 12a and a second ply 12b. The cover material 12 can be formed in any desired shape. Although shown as slightly rectangular in FIG. 1, the cover material 12 can be formed as any regular or irregular polygon or it can be circular or ovoid. Further, the bandage can be formed in any desired size. Thus, the bandage can have dimensions that range from a fraction of an inch to as large as desired. Further, the cover 10 can be a multi-ply cover. That is, inclusive of the peel-away coating or release liner, the cover 10 can be a 2-ply or 3-ply cover. Further, the cover can have 4 or more plies, if desired.

The cover 10, as provided, has at least two plies, a bottom liner ply 15 and an upper ply 12 or cover material which is adhered to the patient. The upper ply 12 includes an adhesive 13 on its bottom surface to removably adhere the two plies together. The bottom ply is removed or separated from the upper ply at the time of application of the cover to the patient, and only the upper ply, as is known, is actually adhered to the patient's skin.

The cover material 12 is made from a pliable, flexible, conformable, breathable material, such as a polymer film. However, it can also be made from cloth, which can be made from synthetic and/or natural materials. The cover material 12 can be stretchable in the machine direction. For example, the cover material can be made from tapes available from 3M under the product numbers 9948 (two-ply) or 9836 (three-ply). These tapes have a top layer formed from a polyester film and a bottom layer formed from a silicone coated paper. The polyester film is coated with an acrylate adhesive and would define the cover material 12 of the adhesive therapeutic cover 10. The top layer is thin—about 0.002" (about 0.05 mm) and has a weight of about 0.13 lbs/ft$^2$. Further, the film is air permeable, but liquid impermeable. These features allow for transpiration and make the film more comfortable to the patient. Finally, the film has a stretchability of about 500% in the machine direction and a minimum tensile strength of about 3 lbs/in (about 0.5 N/mm). The adhesive in this tape has an adhesive strength of about 19 oz/in.

As noted above, the adhesive which adheres the cover material 12 to the patient has an adhesive strength of about 19 oz/in. This is sufficient to hold the cover material 12 to the patient. Yet it is not so strong that it will traumatize the patient's skin upon removal. Stated differently, the strength of the adhesive should be adequate to retain the cover in place for the duration of the wear time. However, the adhesive should permit atraumatic removal, i.e. without causing skin stripping (Rippon, White & Davies, Skin Adhesives and Their Role in Wound Dressings, Wounds UK, 2007 Vol. 3, No. 4, pp. 76-86). For example, the adhesive preferably has a strength greater than about 10 oz/in but less than about 50 oz/in.

At least one lift device 14 extends upwardly from the cover material 12 and places the underside of the cover material 12 in communication with the atmosphere. The lift device 14 is connectable to a source of gas, liquid, flowable gel, or a combination of thereof. The gas, liquid, gel, or combination thereof is referred to as a flowable lifting agent. The flowable lifting agent is preferably sterile. The gas could be air, $CO_2$, or nitrogen, for example. The gel could would be comprised mainly of sterile inactive ingredients, but could be provided with medicaments (such as antimicrobial agents and/or antibacterial agents), wound site cleaning agents (such as iodine), or skin treatments (such as moisturizers) or other flowable agents beneficial to the site on the patient to which the adhesive therapeutic cover is applied. This can also include sterile $O_2$ and sterile saline. Inasmuch as a gas, liquid or flowable gel is used to remove the cover material from the patient's skin, the lifting device can be referred to as a pneumatic or hydraulic removal device.

As described in more detail below, the flowable lifting agent is urged under pressure through the lift device 14 between the adhesive therapeutic cover material 12 and the patient's skin. A motive force is used to break the energy bond between the adhesive and the dermis, separating the adhesively applied cover material from the patient's skin. As noted above, the adhesive which adheres the cover material 12 to the patient is a relatively weak adhesive, and, as the flowable lifting agent is urged through the lift device 14, the flowable lifting agent forms and fills a void space between the cover material 12 and the patient's skin or dermis to lift the cover material 12 off the patient's skin in an ever increasing area. That is, the flowable lifting agent will spread out between the patient's skin and the cover material 12 starting from the area of the lift device 14 and move outwardly towards the edges of the cover material 12 to gently lift and separate the cover material 12 from the patient's skin without unduly traumatizing the patient's skin.

The flowable lifting agent is urged through the lift device 14 between the cover material 12 and the patient's skin at a pressure sufficient to separate the cover material from the patient's skin without unduly traumatizing the patient's skin. For example, if air is used as the flowable lifting agent, the air is urged through the lift device at, for example, a pressure of 2-4 psi for an adhesive having an adhesive strength of 19 oz/in. Additionally, the flowable lifting agent is urged through the lift device at a rate such that the cover material will be slowly, rather than quickly, separated from the patient's skin. For a cover material, such as a 4"×4" (about 10 cm×10 cm) which covers about 16 in2 (~100 cm2) of the patient's skin, the flowable lifting agent is introduced at a rate such that it will take less than one minute to fully remove the cover material from the patient. Larger adhesive therapeutic covers would take longer.

The lift device 14 is shown somewhat generically or schematically in FIG. 2. The lift device 14, as seen therein, includes a tube-like connector 16 adapted to connect the lift device to the source of flowable lifting agent, with a base or flange 16a which extends outwardly from, and surrounds the base of the connector 16. The connector 16 defines a port which is adapted to be connected to the source of lifting agent. The source of lifting agent can be a pump or reservoir (such as a remote tank) which is connected to the connector 16 by a flexible tube. Alternatively, the source of lifting agent can comprise a syringe, which is connected to the connector. The connector can include any conventional means that will enable the lift device to be removably connected to the source of lifting agent. For example, the connector 16 can be a member that extends upwardly (even only slightly) from the therapeutic cover material to enable the cover material to be placed in communication with the source of lifting agent by any conventional means. The source of the lifting agent can thus threadedly connect to the connector 16, or a friction fit could be used (as long as the friction fit is greater than the pressure of the lifting agent), a bayonet type connection, Leuer Lock, etc.

The connector 16 extends upwardly from an attachment apron 18 an opening 19 of the apron 18. The apron 18 has an adhesive on its bottom surface to secure the lift device 14 to the cover material 12. In FIG. 1, the apron 18 is shown to be rectangular or square. However, the apron 18 could be round, triangular, or any other desired shape. The apron 18 can, for example, have a dimension of about 1½" to about 2" (about 3.8 cm to about 5.1 cm). The connector 16 is secured to the apron 18 such that the connector opens through the apron 18. The connector 16 can be secured to the apron 18 in any desired manner, as long as the connection between the connector 16 and the apron 18 will prevent the connector 16 from detaching from the apron during use. For example, the connector 16 can be glued or heat sealed to the apron 18. Alternatively, the connector 16 can include a lower flange 16a at the base of the connector 16 which is adhered to a bottom surface of the apron film 18 and to which the apron 18 is adhered via its adhesive. As seen in FIG. 2, the connector flange 16a is affixed to the bottom surface of the apron 18, and the connector tube 16 extends though the opening 19. Alternatively, the connector flange 16a could be affixed to the top surface of the apron, such that the connector tube 16 is in alignment with the apron opening. As another alternative, the connector 16 and apron 18 can be formed as a one-piece unitary member. This would eliminate the need for the flange 16a.

The lift device 14 is adhered to the cover material 12 such that the tube-like connector 16 is aligned with a window or access port 20 in the cover material 12. The port 20 can be a pre-existing opening or hole in the cover material, through which the patient's skin is exposed. Alternatively, the access port 20 can be defined by a removable section of the cover material 12, such that the cover material 12 at the port can be removed for application of the lift device 14. This would allow for application of the lift device 14 to the cover material after that cover material has been applied to the patient and at the time for removal of the cover material. This may be more comfortable for the patient when the bandage is to be worn for an extended period of time. In this instance, the port 20 can be similar to the windows described in conjunction with FIG. 28 of the above noted PCT Pub. No, WO 2014/120746, which is incorporated herein by reference. To prevent the lift device 14 from separating from the cover material during use, the adhesive of the apron 18 is stronger than the adhesive of the cover material 12. For example, the adhesive for the apron can have a strength of about 50 oz/in.

An acceptable material for the apron 18 is a film available from 3M under product number 1516. This is a heat sealable material that can be bonded to the connector 16. This film has an elongation factor that is substantially less than the elongation factor of the cover material 12. For example, the apron can have an elongation factor of 50%. Because the apron film adhesive is substantially stronger (at least 50% stronger) than the cover material adhesive, the pressure exerted by the flowable lifting agent will not separate the lift device 14 from the cover material 12. Further, because the apron film 18 is substantially less stretchy than the cover material 12, cover material 12 will not "balloon out" in the area of the apron film 18. Rather, the initial lifting agent urged through the connector 16 will separate the cover material 12 from the patient's skin to form an initial separation area that expands as further flowable lifting agent is passed through the connector 16 into the separation area between the cover and the patient's skin.

FIG. 3A shows an embodiment of the cover in which the lift device 14 is affixed to the cover 10 as supplied (i.e., by the manufacturer). In FIG. 3A, the connector 16 includes the flange or base 16a, but the apron is omitted. Further, the connector 16 is shown to be an externally threaded tube. In this embodiment, the access hole 20 is formed in of the cover material 12 and is sized to allow the connector 16 to pass therethrough. The connector flange 16a is adjacent the underside of the cover material 12 to be adhered in place by the adhesive of the cover material. The bottom ply 12b15 (which is a release liner) is applied to the bottom surface of the cover material and the connector, such that in the as supplied condition, the bottom ply 15 will cover (and thus closes) the bottom surface of the flange 16a.

Figure 3B:
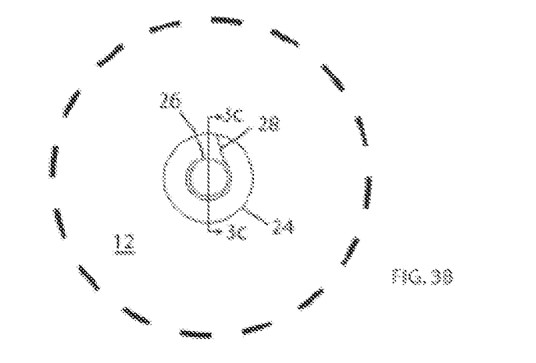
FIGS. 3B and 3C are top plan and cross-sectional views of the second embodiment of the lift device, with FIG. 3C being taken along line 3C-3C of FIG. 3B, demonstrating a second method of securing the lift device to the cover.
Figure 3C:
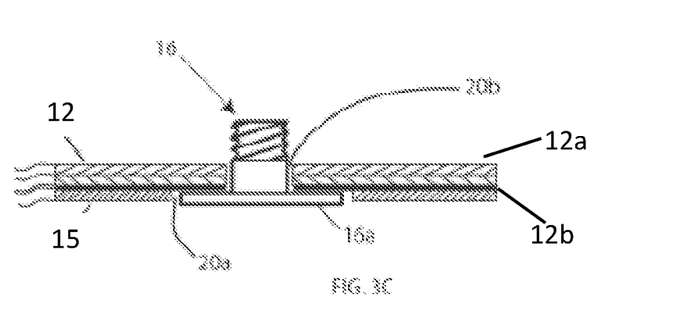

FIGS. 3B and 3C show a cover wherein the lift device 14 is supplied separately from the cover, but is to be applied or affixed to the cover material 12 prior to application of the cover material to the patient. The connector 16 shown in FIGS. 3B and 3C is identical to the connector of FIG. 3A, and will not be further described. The cover of FIGS. 3B and 3C, is formed to allow the medical personnel to manually adhere the connector 16 to the cover. The cover is shown to be formed from a 3-ply film (i.e., the cover material 12 has two layers or plies, and the release line 15 has one layer or ply) which is provided with an openable access aperture 20 defined by an outer bottom cut 24 (which extends only through the release liner 15) and an inner top-middle cut 26 that is concentric with the outer bottom cut 24 (and extends through both plies of the cover material 12, i.e., the top and middle plies). The outer bottom cut 24 is sized to form a hole 20a in the release liner 15 which will accept the flange 16a of the connector 16. The inner, top-middle cut 26 is sized to form a hole 20b in the plies of the cover material sized to admit the connector 16 to pass therethrough. The top-middle cut 26 defines a "push tab" which when pressed (i.e., pushed downwardly or through the release liner), will separate the plies of the cover material below the push tab, and the release liner, to form the holes 20a,b in the cover prior to removal of the release liner 15 from the cover material 12 of the cover. As can be appreciated, the holes 20a,b in combination define the access aperture 20. Opening the access aperture 20 as just described will expose the adhesive of the middle ply 14 around the opening 20a, and the base/flange 16a of the connector can be pressed against the bottom of the middle ply in the hole 20a to adhere the connector 16 in place in the cover. The cuts 24,26 are formed such that, if the connector 16 is not going to be used, the respective plies of the cover will remain contiguous, that is, the portion of the release liner 15 surrounded by the cut 20a will be removed with the rest of the release liner. The cuts 20a,b could, for example, be perforated cuts, rather than continuous cuts. In addition, the cover includes a scythe-shaped cut 28, comprising a leg which extends from the outer cut 24 towards the inner cut 26. This leg is not a radially extending cut, but rather defines an acute angle with a diameter of the two cuts. An arced cut then extends from the end of this leg, and substantially surrounds the inner cut 26. The scythe-shaped cut 28 helps with the removal of the material to open the access port hole 20.

Figure 4A:
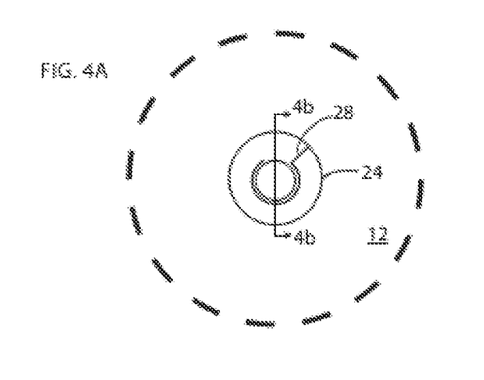
FIGS. 4A and 4B are fragmentary and cross-sectional views, respectively, of a variation from the cover of FIG. 3A for forming an access port in the cover, with FIG. 4B being taken along line 4B-4B of FIG. 4A.
Figure 4B:
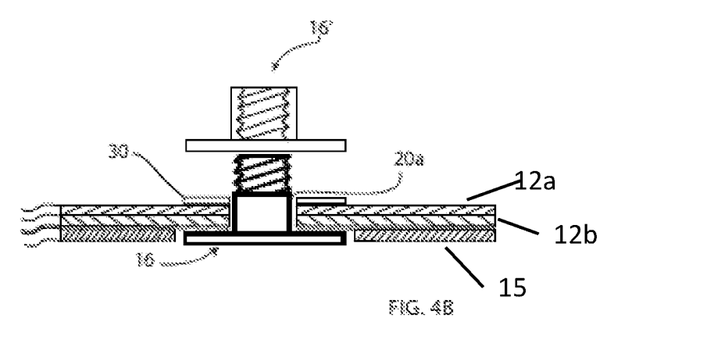

The cover of FIGS. 4A and 4B is provided with access port aperture 20 identical to the access port aperture 20 of FIG. 3A,B. The cover of FIG. 4A,B also includes an anti-friction washer 30 which surrounds the access port aperture hole 20a to reduce abrasions. Additionally, the cover is shown, in FIG. 4B, with both the externally and internally threaded connectors 16 and 16', respectively. The internally threaded connector can be used in lieu of the externally threaded connector. Alternatively, the internally and externally threaded connectors can be used together. In this instance, one connector is threaded into (or onto) the other, such that the cover top ply(s) is(are) sandwiched between the flanges of the two connectors. The connector can be fixed to the cover by any desired suitable connection method, i.e., twist lock, friction, quick connect, etc. Alternatively, the flange of the connector could be heat sealed to the substrate.

Figure 5A:
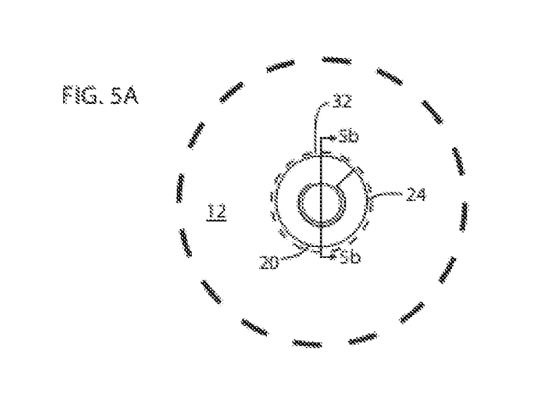
FIGS. 5A and 5B are fragmentary and cross-sectional views, respectively, of a variation of the cover of FIGS. 4A and 4B, with FIG. 5B being taken along line 5B-5B of FIG. 5A.
Figure 5B:
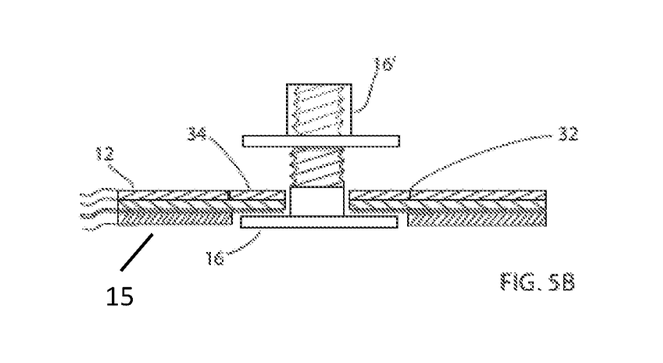

The cover of FIGS. 5A and 5B is substantially similar to the cover of FIG. 4A,B. However, the cover of FIG. 5A,B is provided with a perforated cut 32 in the top ply around the port assembly aperture 20 which is approximately equal in diameter to the bottom cut 24 of the port assembly aperture. When the top ply 12a of this cover is removed from the middle ply 12b, the top ply within the top perforated cut 32 can remain with the middle ply to define the anti-friction washer 34. Thus, the cover of FIG. 5A,B provides for the anti-friction washer without the need for an additional manufacturing step.

Due to various factors, the separation area may not grow at an even pace. Thus, even if the lift device 14 is located centrally (side-to-side) on the cover material 12, the separation area may reach one side of the cover material before it reaches the other side. If this happens, the flowable lifting agent may separate an area of one edge of the cover material 12 from the patient before the cover material 12 is substantially fully separated from the patient. If such a separation forms, additional flowable lifting agent may not further separate the film 12 from the patient's skin; rather, the flowable lifting agent may simply flow out the separation that was formed at the edge of the cover 12. To help reduce the possibility of such an edge separation or edge leak from forming, the adhesive therapeutic cover 10 can be provided with a reinforcing border 22. This reinforcing border 22 can be made of the same material as the cover material 12, such that it has the same properties, including the same elongation factor, as the cover material 12. Alternatively, the border 22 can be made of a different material than the cover material 12. For example, the border 22 can be made from 3M film identified under product number 9865. This film has an elongation factor of 200% which is less than the elongation of the cover material 12. Additionally, the 3M 9865 film is a non-breathable film that has a thickness of 0.11 mm (which is about twice the thickness of the cover material 12). In either instance, the border 22, when adhered to the cover material 12 will reduce the stretchability of the adhesive therapeutic cover 10 at the edge of the cover material beneath the border 22. The border 22 can have a width W that is about 10% of the dimension of the adhesive therapeutic cover 10. For a large cover, for example, greater than about 10"×10" (about 25×25 cm), the border can be at least about 1" (~2.5 cm) wide. For even larger covers, the border can be about 2" (~5 cm) to about 3" (~7½ cm) wide. Because the cover is less stretchable beneath the border 22, when the lifting agent reaches the border 22 at a portion of the cover material 12, the area of separation between the cover material 12 and the patient's skin will grow in an area of the bandage remote from that portion of the border, to reduce the possibility of an edge gap from forming through which lifting agent could escape.

Although the lift device 14 is described with respect to an adhesive therapeutic cover in the form of a bandage, the lift device can also be used with a therapeutic covers such as the retractors disclosed in WO 2014/120746 and with wound exposure devices, such as are disclosed in International App. No. PCT/US2016/013404, both of which are incorporated herein by reference. With the much larger area of the retractor or wound exposure device, it may be necessary for the covering to have two, three, four, five, or even more lift devices, and the multiple lift devices would then be placed at desired positions on the covering. In addition, as noted above, the adhesive therapeutic cover can also be used in conjunction with surgical or cosmetic procedures. Broadly stated, "adhesive therapeutic cover" is defined as a pliable, conformable substrate which having an adhesive which adheres the substrate to a patient's skin and which includes at least one lifting device 14 to separate the substrate (cover material) from the patient's skin.

One use of the therapeutic cover 10 may be post-surgical to cover a closed incision. The adhesive therapeutic cover would maintain the incision closed during healing and thus will reduce the size of any scar that is formed while the incision heals.

A less apparent use of the adhesive therapeutic cover 10 is in conjunction with burn victims or skin grafts. In such instances, the conventional wisdom is that any adhesive applied to newly formed skin will damage the newly formed skin. However, the lifting device 14 allows for separation of an adhesive therapeutic cover 10 from newly formed skin without substantially damaging the skin/graft. This is accomplished by use of a weak adhesive (as described above) and a low pressure application of the lifting agent. Further, in such instances, the adhesive is preferably impregnated with anti-microbial, anti-bacterial, and/or other agents, such as EGF (epidermal growth factor), which facilitates growth of new skin while the burn area or the graft is covered by the cover material 12. In addition, in such situations, a gel which includes anti-microbial, anti-bacterial or other skin treating agents can be used as the lifting agent. This will enable the area covered by the cover material 12 to be coated with a treating agent before the skin is exposed to air. Further, because the cover material 12 is air permeable, the cover material 12 allows for transpiration necessary for the formation and healing of the new skin/skin graft. Finally, once applied, the burn site or skin graft site can be prepped right over the cover material 12.

In such instances, the cover material can be made from a non-plastic material such as gauze, cotton, etc. In this case, when the cover is previously affixed to a patient and is difficult to remove, a drape, can simply be placed over the existing wound covering to lift it off.

As noted above, the cover, as a bandage, must be removed carefully, so as to reduce the possibility of damaging sensitive skin. To this end, the cover can be provided with one or more sensors S which can be used to monitor pressure between the skin and the cover, as lifting agent is urged through the connector 16. Monitoring pressure would also indicate when a gap forms at the edge of the cover. A gap would be detected by a drop in the pressure under the cover 12. Additionally, sensors could be provided to monitor the flow of lifting agent through the connector. Additionally, a sensor could be provided in the reinforcing border. This border sensor would detect when the flowable lifting agent reaches the border and could be used to control the flow of lifting agent through the port. Specifically, the detection of lifting agent at the border can signal a controller to abate the amount of flowable lifting agent through the port.

Thus, as can be appreciated, the sensors can communicate with (send a signal to) a controller which, in turn, controls the flow of lifting agent through the connector in response to the signal from the sensors. Alternatively, the sensor can communicate with a receiver which receives the signal from the sensor. The receiver can then provide a warning (such as with a warning light or audible alarm) if the detected parameter exceeds a predetermined threshold (for example the pressure or flow rate is too great). This would indicate that the cover is being removed from the patient at too fast a rate. The receiver could also issue a warning if the detected parameter (i.e., pressure) drops. A pressure drop could indicate that a gap has formed at an edge of the cover through which lifting agent is escaping.

As various changes could be made in the above constructions without departing from the scope of the invention, it is intended that all matter contained in the above description or shown in the accompanying drawings shall be interpreted as illustrative and not in a limiting sense. For example, the lift device 14 can be a separate element that is secured to the cover material 12 when it is time to remove the cover material from the patient. Alternatively, the lift device 14 can be pre-applied to the cover material 12 to be part of the adhesive therapeutic cover 10, as supplied. In this latter instance, the connector 16 could be adhered directly to the cover material 12 at the site of the opening 20. Although the connector 16 is disclosed to be adhered to the cover material 12 via the apron film 18, the connector 16 could be fixed directly to the cover material 12, such as by gluing, welding, or otherwise bonding the connector 16 to the cover material 12. In this instance, the connector would be adhered directly to the cover 12. For example, the connector flange 16a can be adhered to the bottom surface of the cover 12, and the connector tube 16 can then extend through the opening 20 in the cover 12. The lift agent is described as a gas or a flowable gel. However, the lift agent could also be a liquid. Such a liquid would preferably be sterile, and could include medicaments or skin treating agents. Any of the connectors 16 shown in the drawings can be used with any of the covers. These examples are merely illustrative.

The invention claimed is:

1. A therapeutic cover comprised of:
a single sheet of material having at least a cover material and a backing layer; the cover material being made of a pliable, conformable material and sized to cover a wound, said wound being a surgical incision, a burn, or a skin graft; said cover material having an adhesive applied to a bottom surface thereof to removably adhere the cover material and backing layer together; said adhesive covering substantially the entire bottom surface of said cover material and being adapted to enable the cover material to be adhered to the skin of a patient; the cover material defining at least one opening therethrough or at least one opening area which can be removed after application of the cover material to a patient to form an opening through the cover material; a dimension of said cover material being at least twice as large as a dimension of said at least one opening; and
at least one lift device adapted to cover said opening, said at least one lift device comprising a hollow connector aligned with the at least one opening or at least one opening area and being adapted to be connected to a pressurized source of a flowable lifting agent; said connector being adhered or adherable to the cover material to extend upwardly from a top surface of the cover material, said connector being in communication with a bottom surface of said cover material when adhered to said cover material;
whereby said cover is configured such that when the cover is applied to a patient's skin, said flowable lifting agent can be urged through said connector and said opening in said cover material to lift said cover material adhered to the patient by said adhesive from patient skin after application of the cover material to patient skin.

2. The therapeutic cover of claim 1 wherein said lift device comprises an apron which surrounds said connector, and to which said connector is fixed; said apron being fixed to the cover material.

3. The therapeutic cover of claim 2 wherein said apron is adhered to said cover material by an adhesive or bond which is stronger than the adhesive of the cover material.

4. The therapeutic cover of claim 3 wherein said opening is positioned approximately midway between opposite sides of said bottom surface of said cover material.

5. The therapeutic cover of claim 4 wherein said border is comprised of a material that is adhered to the cover material.

6. The therapeutic cover of claim 5 wherein said border has a thickness greater than a thickness of said cover material.

7. The therapeutic cover of claim 6 wherein said border is approximately 1× to 2× as thick as the cover material.

8. The therapeutic cover of claim 6 wherein said material from which said border is made has an elongation factor that is less than an elongation factor of said cover material.

9. The therapeutic cover of claim 2 wherein said apron is secured to said cover material by an apron adhesive or bond; said adhesive being a stronger adhesive than the adhesive on the bottom surface of the cover material.

10. The therapeutic cover of claim 9 wherein said apron adhesive or bond is at least equal to or greater than the strength of said adhesive of said cover material.

11. The therapeutic cover of claim 10 wherein said border is about 0.5" (~1.3 cm) to about 3" (~7.5 cm) wide.

12. The therapeutic cover of claim 10 wherein said material from which said border is made is a non-breathable material.

13. The therapeutic cover of claim 2 where said apron is made of a material having an elongation factor that is less than an elongation factor of the cover material.

14. The therapeutic cover of claim 13 wherein said apron has an elongation factor that is no more than about 75% of the elongation factor of the cover material.

15. The therapeutic cover of claim 14 wherein said apron has an elongation factor of about 0% to about 200%.

16. The therapeutic cover of claim 1 wherein said cover material is comprised of a manmade material, natural material, or combination thereof.

17. The therapeutic cover of claim 16 wherein the cover material is formed from a breathable or non-breathable material.

18. The therapeutic cover of claim 17 wherein the cover material is typically formed from a thermoplastic elastomer.

19. The therapeutic cover of claim 18 wherein the thermoplastic elastomer is a polyester or a polyurethane.

20. The therapeutic cover of claim 16 wherein the cover material is formed from a non-plastic material.

21. The therapeutic cover of claim 20 wherein the cover material is formed from gauze or cotton.

22. The therapeutic cover of claim 1 including at least one sensor which detects a parameter of the flowable lifting agent; said at least one sensor sending a signal indicative of the parameter being sensed to facilitate control of the flowable lifting agent through the connector.

23. The therapeutic cover of claim 22 wherein the at least one sensor detects a flow rate of the flowable lifting agent through or a pressure of lifting agent beneath the cover.

24. The therapeutic cover of claim 23 wherein the at least one sensor is proximate the connector.

25. The therapeutic cover of claim 23 wherein the at least one sensor comprises a border sensor proximate the border, said border sensor being adapted to detect when the flowable lifting agent reaches the border.

26. The therapeutic cover of claim 22, including a controller, said controller receiving a signal from the at least one sensor, said controller controlling a flow of the flowable lifting agent through the connector in response to the signal from the at least one sensor.

27. The therapeutic cover of claim 22, wherein said signal is transmitted to a receiver, said receiver issues a visual and/or audio warning if a detected parameter exceeds a predetermined threshold.

28. The therapeutic cover of claim 1 wherein the at least one lift device includes a port member extending upwardly from a flange which surrounds the port member; said port member being adapted to be connected to the pressurized source of said flowable lifting agent.

29. The therapeutic cover of claim 28 wherein the cover material is sufficiently clear such that UV light used to treat chronic wound or active infection in wound can be transmitted through the cover material.

30. The therapeutic cover of claim 1 wherein the adhesive has an adhesive strength sufficiently low so as to substantially prevent trauma to human skin when the cover material is removed from human skin.

31. The therapeutic cover of claim 30 wherein the adhesive has a strength of about 10 oz/in to about 50 oz/in.

32. The therapeutic cover of claim 1 wherein said flowable lifting agent is a gas, liquid, flowable gel, or a combination thereof.

33. The therapeutic cover of claim 32 wherein said lifting agent comprises a medicament and/or a skin treating agent.

34. The therapeutic cover of claim 1 further including a border extending around a periphery of the cover material.

35. The therapeutic cover of claim 34 wherein said border is an adhesive border, wherein the adhesive of the cover material is a first adhesive, and the adhesive border is defined by a second adhesive applied to the cover material around the periphery of the cover material, the second adhesive being stronger than the first adhesive.

36. The therapeutic cover of claim 1 wherein the cover material has a thickness of about 1.2 mils.

37. The therapeutic cover of claim 1 wherein the therapeutic cover is supplied with the lift device already adhered to the cover material.

38. The therapeutic cover of claim 1 including at least one sensor which detects ambient and physiological aspect of a patient's wound.

39. A method of removing a therapeutic cover that has been adhered by means of an adhesive to a patient's skin wherein the therapeutic cover is adhered to the patient's skin substantially over the entire area of the therapeutic cover; the therapeutic cover comprising:
  a single sheet of material having at least a cover material and a backing layer; the cover material being made of a pliable, conformable material and sized to cover a wound, said wound being a surgical incision, a burn, or a skin graft; said cover material having an adhesive applied to a bottom surface thereof to removably adhere the cover material and backing layer together; said adhesive covering substantially the entire bottom surface of said cover material and being adapted to enable the cover material to be adhered to the skin of a patient; the cover material defining at least one opening therethrough or at least one opening area which can be removed before or after application of the cover material to a patient to form an opening through the cover material; a dimension of said cover material being at least twice as large as a dimension of said at least one opening; and
  at least one lift device adapted to cover said opening, said at least one lift device comprising a hollow connector aligned with the at least one opening or at least one opening area and being adapted to be connected to a pressurized source of a flowable lifting agent; said connector being adhered or adherable to the cover material to extend upwardly from a top surface of the cover material, said connector being in communication with a bottom surface of said cover material when adhered to said cover material;
  whereby said cover is configured such that when the cover is applied to a patient's skin, said flowable lifting agent can be urged through said connector and said opening in said cover material to lift said cover material adhered to the patient by said adhesive from patient skin after application of the cover material to patient skin;
  the method comprising a step of introducing a flowable lifting agent under pressure through the lift device between the therapeutic cover and the patient's skin at a rate and pressure sufficient to lift the adhered therapeutic cover from the patient's skin, the rate and pressure being selected to substantially eliminate the possibility of damaging or injuring the patient's skin while removing the adhesive therapeutic cover from the patient's skin.

40. The method of claim 39 wherein said flowable lifting agent is a gas, a liquid, a flowable gel or a combination thereof.

41. The method of claim 40 wherein said flowable lifting agent contains medicaments and/or skin treating agents.

42. The method of claim 39 wherein said therapeutic cover comprises at least one connector extending upward from said therapeutic cover; said at least one connector being in communication with an underside of said therapeutic cover through an aperture in said therapeutic cover; said step of introducing the flowable lifting agent between a bottom surface of the therapeutic cover and the patient's skin comprising passing said flowable lifting agent through said at least one connector under pressure via a motive force.

43. The method of claim 39 wherein said flowable lifting agent is introduced at a pressure of about 2-4 psi.

44. The method of claim 39 wherein said flowable lifting agent dissipates the energy of the adhesive bond securing the therapeutic cover to the patient's skin, thereby causing separation of the therapeutic cover from the patient's skin.

45. A therapeutic cover comprised of:
  a single sheet of material having at least a cover material and a backing layer; the cover material having an adhesive applied to a bottom surface thereof to removably adhere the cover material and backing layer together; the adhesive being adapted to enable the cover material to be adhered to the skin of a patient; the cover material defining at least one opening therethrough or at least one opening area which can be removed after application of the cover material to a patient to form an opening through the cover material; said adhesive substantially covering the entire bottom surface of said cover material; and
  at least one lift device, said at least one lift device comprising a connector aligned with the at least one opening or at least one opening area and being adapted to be connected to a pressurized source of a flowable lifting agent; said connector being adhered or adherable to the cover material to extend upwardly from a top surface of the cover material,
  whereby said cover is configured such that when the cover is applied to a patient's skin, said flowable lifting agent can be urged through said connector and said opening in said cover material to lift said cover material adhered to the patient by said adhesive from patient skin after application of the cover material to patient skin;
  wherein the at least one lift device is supplied separately from the therapeutic cover; the therapeutic cover further including an access port defined by a cut in the cover material forming a closed shape, said cut being formed such that the material within the closed shape can be removed to thus define an access port; the lift device including a flange/apron which can secure the lift device over the access port with a port member of the lift device in alignment with the access port in the cover material.

46. The therapeutic cover of claim 45 wherein the cover material is formed from at least a two-ply material comprising an upper ply and a lower ply; said access port being defined by an inner cut in said upper ply and a larger bottom cut in the lower ply which surrounds the inner cut in the upper ply, said larger bottom cut defining a hole in said lower ply sized to receive the flange/apron of said at least one lift device, and said inner cut in the upper ply defining a hole sized to allow passage of said port member therethrough, whereby said access port is formed by removing the material inside of said larger bottom cut and inner cut from said cover material, and said at least one lifting device is connected to the cover material prior to placing of the therapeutic cover on the patient.

\* \* \* \* \*